United States Patent [19]
Miller et al.

[11] Patent Number: 5,900,534
[45] Date of Patent: May 4, 1999

[54] DENSITOMETER

[75] Inventors: Charles E. Miller, Boulder; James Foster; Thomas Smith, both of Longmont, all of Colo.

[73] Assignee: Natural Fuels Corporation, Denver, Colo.

[21] Appl. No.: 08/726,942

[22] Filed: Oct. 7, 1996

[51] Int. Cl.[6] .................................................. G01F 1/68
[52] U.S. Cl. ...................................... 73/24.05; 73/861.01
[58] Field of Search ............................... 73/24.01, 24.05, 73/32 A, 861.351, 861.352, 861.01

[56] References Cited

U.S. PATENT DOCUMENTS

| | | | |
|---|---|---|---|
| 2,754,676 | 7/1956 | Poole | 73/32 A |
| 3,420,092 | 1/1969 | Dorsch | 73/24.05 |
| 3,516,283 | 6/1970 | Abbotts | 73/32 A |
| 3,618,360 | 11/1971 | Curtis | 73/24.05 |
| 3,874,221 | 4/1975 | Lockie | 73/24.05 |
| 4,240,285 | 12/1980 | Langdon | 73/32 A |
| 4,453,401 | 6/1984 | Sidey | 73/754 |
| 4,546,641 | 10/1985 | Nguyen | 73/32 A |

*Primary Examiner*—Ronald L. Biegel
*Attorney, Agent, or Firm*—James R. Young; Chrisman, Bynum & Johnson, P.C.

[57] ABSTRACT

A densitometer (10) includes a gas sample plenum (40) that is connected to a gas supply pipe (26) via a flow-restricted inlet duct (42) to at least partially isolate and damp the sample plenum (40) from shocks and noises, turbulences, and abrupt pressure changes in the gas supply. A cantilevered vane (110) is positioned in the sample plenum (40) for gas density determinations on the principle that resonant frequency of the vane (110) is a function of the density of the gas in the sample plenum (40). The resonant frequency of the vane (110) in the gas is determined by applying a magnetic field generated by a driver assembly 120 against the vane (110) and detecting the resonant frequency with a vibration detector (117), which is connected to the driver assembly 120 in a phase locked loop.

29 Claims, 14 Drawing Sheets

DENSITOMETER

INCORPORATION BY REFERENCE OF RELATED PATENTS

This patent application incorporates by reference the entire invention disclosure and description in U.S. Pat. No. 5,564,306, issued Oct. 15, 1996 and in U.S. Pat. No. 5,238,030, issued Aug. 24, 1993.

BACKGROUND OF THE INVENTION

1. Field of the Invention

This invention relates generally to density measuring devices and more specifically to a method and apparatus for measuring density of a flowing compressible gas on a real time basis.

2. State of the Prior Art

There are many reasons for measuring density of a flowing compressible gas. One example is in dispensing and measuring compressed natural gas (CNG) into a customer's vehicle tank at the point of sale. As explained in U.S. Pat. No. 5,238,030, which is incorporated herein by reference, mass flow rate $\dot{m}$ of natural gas can be measured quite accurately with a mass flow meter comprising a sonic nozzle. At a given gas temperature and pressure at the entrance of a sonic nozzle, i.e., a nozzle in which flow is choked, the mass flow rate $\dot{m}$ of the gas flowing through the nozzle remains constant regardless of variations in pressure downstream of the nozzle. Therefore, by knowing some information about the specific sonic nozzle being used, including the nozzle discharge coefficient Cd and the cross-sectional area of the nozzle throat $A_t$, by measuring stagnant pressure $P_o$ and temperature $T_o$ of the gas immediately upstream of the sonic nozzle, and knowing the specific heat ratio k and the universal gas constant R of the gas, the mass flow rate $\dot{m}$ of the gas flowing through the nozzle can be determined according to the relationship:

$$\dot{m} = C_d \frac{kA_t P_0}{\sqrt{RT_0}}$$

However, natural gas does not always have the same molecular composition, thus also does not always have the same specific heat ratio k, which can vary. Consequently, mass flow rate $\dot{m}$ determinations according to the relationship above is not always accurate, if the specific heat ratio k is presumed to be constant when it really varies.

The modified sonic nozzle flow dispenser for compressed natural gas (CNG) described in U.S. Pat. No. 5,564,306, issued Oct. 15, 1996 which is also incorporated herein by reference, provides a method and apparatus for determining specific heat ratio k of the natural gas on a real time basis as the natural gas flows through the sonic nozzle. In that invention, the specific heat ratio k is determined as a function of the ratio of a gas pressure $P_i$ inside the nozzle to the gas pressure $P_o$ immediately upstream of the nozzle. Mass flow rate $\dot{m}$ can then be determined by measuring the density $\rho_o$ of the natural gas at the stagnant pressure $P_o$ immediately upstream of the sonic nozzle and then calculating the mass flow rate $\dot{m}$ as a function of the density $\rho_o$, the pressure ratio ($P_i/P_o$), and the specific heat ratio k.

There are a number of good densitometers that can be used to determine the density $\rho_o$ of the natural gas for the purpose of calculating mass flow rate $\dot{m}$ in CNG dispensers as described above or for any number of other purposes. However, such state-of-the-art densitometers that can produce accurate enough density measurements on a real time basis for use in accurate measurements of mass flow rate $\dot{m}$ in natural gas dispensers where customers are charged for the natural gas according to such measurements tend to be very expensive and difficult to install in a manner that measures gas density $\rho_o$ at the stagnant pressure $P_o$ immediately upstream of the sonic nozzle. Space requirements, noise and pressure fluctuations, and sensitive densitometer components make it difficult and expensive to obtain accurate gas density $\rho_o$ measurements in these circumstances.

SUMMARY OF THE INVENTION

Accordingly, it is an object of this invention to provide an accurate, but relatively inexpensive densitometer for measuring gas density on a real time basis.

It is also an object of this invention to provide a densitometer that can measure density of a flowing gas accurately in a noisy, turbulent, vibrating environment.

A more specific object of this invention is to provide a densitometer that can measure gas density accurately at a stagnant pressure on a real time basis immediately upstream of a sonic nozzle flow meter in a gas dispenser as gas flows through the dispenser.

Additional objects, advantages, and novel features of the invention shall be set forth in part in the description that follows, and in part will become apparent to those skilled in the art upon examination of the following or may be learned by the practice of the invention. The objects and the advantages may be realized and attained by means of the instrumentalities and in combinations particularly pointed out in the appended claims.

To achieve the foregoing and other objects, and in accordance with the purpose of the present invention as embodied and broadly described herein, the apparatus of this invention for measuring density of a flowing gas accurately and on a real time basis generally includes a sample plenum connected to a source of gas, an elongated, cantilever mounted vane extending into said sample plenum, driver means positioned adjacent the vane for imparting vibrating motion in the vane, and a vibration detector connected to the vane.

To achieve the foregoing and other objects, and in accordance with the purpose of the present invention as embodied and broadly described herein, the method of this invention for measuring density of a flowing gas accurately and on a real time basis generally includes diverting a portion of a flow of gas from a gas supply chamber through an inlet duct to a sample plenum, measuring the density of the gas in the sample plenum by detecting resonant frequency of a cantilevered vane extending into the sample plenum, and flowing the gas out of the sample plenum downstream of the gas supply chamber. The method includes damping noises, turbulences, and abrupt pressure changes by flowing the gas through an inlet duct that is restricted in size.

BRIEF DESCRIPTION OF THE DRAWINGS

The accompanying drawings, which are incorporated herein and form a part of this specification illustrate the preferred embodiment of the present invention, and together with the description, serve to explain the principles of the invention.

In the drawings

DETAILED DESCRIPTION OF THE PREFERRED EMBODIMENTS

Figure 1:
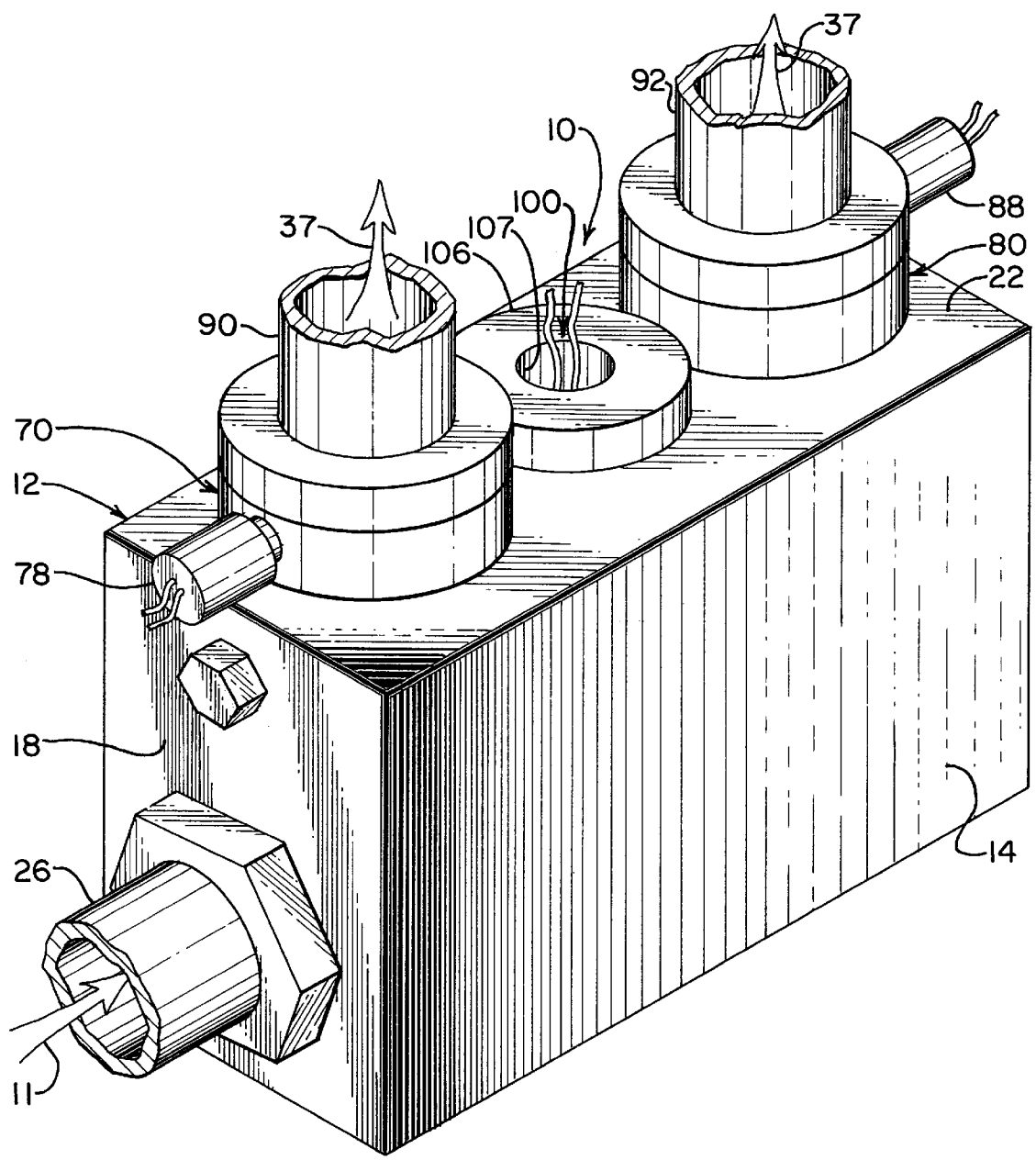
FIG. 1 is an isometric view of the densitometer housing of the present invention in combination with two sonic nozzle gas dispenser mass flow meters mounted on the housing.
Figure 2:
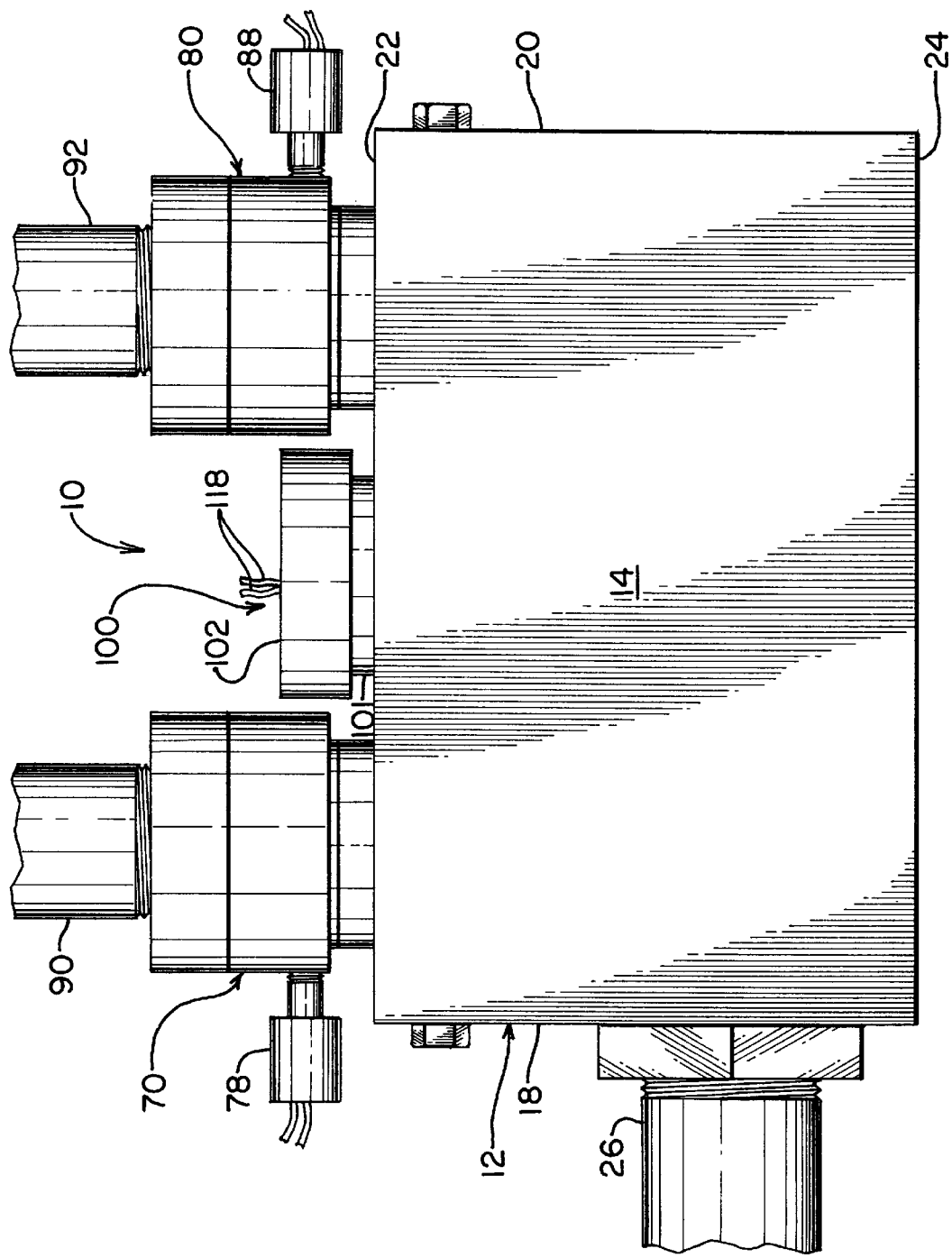
FIG. 2 is a front elevation view of the densitometer housing of FIG. 1.
Figure 3:
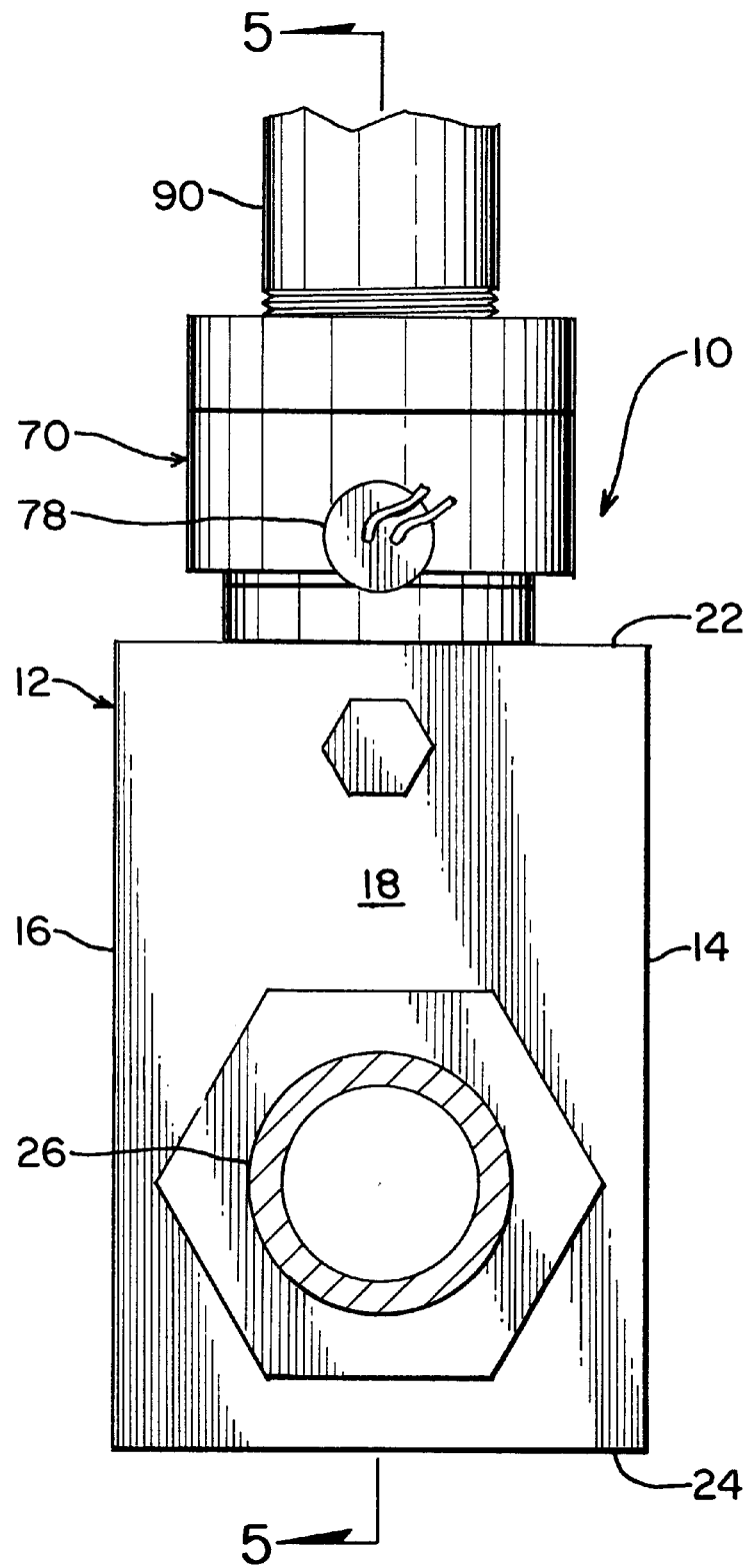
FIG. 3 is an end elevation view of the densitometer housing of FIG. 1.

A densitometer apparatus 10 according to the present invention is shown in FIG. 1 connected to a compressed natural gas (CNG) supply pipe 26, from which gas can flow into the densitometer apparatus 10 as indicated by arrow 11. Two separate gas dispenser pipes 90, 92 are illustrated connected to a respective first sonic nozzle metering assembly 70 and a respective second sonic nozzle metering assembly 80, as would be used in a natural gas dispensing system that is configured to dispense natural gas into two different vehicle tanks (not shown) or similar uses. Such natural gas dispensers that utilize sonic nozzle flow meters are described in more detail in U.S. Pat. No. 5,238,030 and U.S. Pat. No. 5,564,306, issued Oct. 15, 1996 although specific natural gas dispenser structures or embodiments are not essential to this invention. Therefore, such natural gas dispenser apparatus as valves, controllers, vehicle tanks, and other components of such systems are not shown or described in this specification. However, because the densitometer apparatus 10 of this invention is particularly useful for providing gas density measurements for use in more accurate mass flow rate $\dot{m}$ measurements with sonic nozzle flow meters as described in U.S. Pat. No. 5,564,306, issued Oct. 15, 1996 the sonic nozzle metering assemblies 70, 80 are shown and described in general terms as an aid to understanding the structure and advantages of ths invention.

As shown in FIGS. 1–4, the densitometer apparatus 10 includes a housing 12, which can, but does not have to be, shaped as a rectangular solid with a front side 14, back or rear side 16, left end 18, right end 20, top 22, and bottom 24. Then, referring primarily to FIGS. 5 and 6 in combination with FIGS. 1–4, gas, such as compressed natural gas (CNG), from the supply pipe 26 flows into a large manifold bore 30. A first staging plenum 32 and a second staging plenum 34 are connected to the manifold bore 30, so that the gas flows from the manifold bore 30 into the staging plenums 32, 34 as indicated by the respective arrows 33, 35. When valves (not shown) are opened to dispense gas from either or both of the dispenser pipes 90, 92, the gas flows from the respective staging plenums 32, 34 through the respective first sonic nozzle metering assembly 70 and/or second sonic nozzle metering assembly 80 to the respective dispenser pipes or outlets 90, 92, and to a suitable receptacle (not shown) as indicated by respective arrows 37, 39. As described in more detail in U.S. Pat. No. 5,238,030, and in U.S. Pat. No. 5,564,306, issued Oct. 15, 1996, when there is a sufficiently high pressure ratio between the stagnation pressure $P_o$ in the staging plenum 32 or 34 upstream of the respective nozzle 72 or 82 and the pressure $P_1$ downstream of the respective nozzle 72 or 82, the gas flow through the nozzle 72 or 82 is choked. In such choked or critical flow condition, the mass flow rate $\dot{m}$ remains constant for a given upstream pressure $P_o$ and gas temperature $T_o$, regardless of variations in downstream pressure $P_1$. Each nozzle 72, 82 has a respective throat 75, 85 between a respective converging section 73, 83 and a respective diverging section 74, 84.

As also explained in U.S. Pat. No. 5,564,306, issued Oct. 15, 1996, more accurate mass flow rate $\dot{m}$ measurements of a flowing natural gas that varies in molecular composition can be made by first using a pressure $P_i$ measured near the throat 75 or 85 of the sonic nozzle 72 or 82 in choked flow condition along with the upstream stagnant pressure $P_o$, the cross-sectional area $A_i$ of the nozzle 72 or 82 where the pressure $P_i$ is measured, and the cross-sectional area $A_t$ of the throat 75 or 85 to determine specific heat ratio k of the gas from the formula $$\sqrt{1-\left(\frac{P_i}{P_0}\right)^{\frac{k-1}{k}}} = \left[\frac{A_t}{A_i}\left(\frac{2}{k+1}\right)^{\frac{1}{k-1}}\sqrt{\frac{k-1}{k+1}}\right]\left(\frac{P_i}{P_0}\right)^{-\frac{1}{k}} \quad (1)$$

and then using the specific heat ratio k and the density $\rho_o$ of the gas at the pressure $P_o$ along with the pressures $P_o$ and $P_i$ and cross-sectional area $A_i$ to determine the mass flow rate $\dot{m}$ according to the formula $$\dot{m} = A_i\left[\rho_0\left(\frac{P_i}{P_0}\right)^{\frac{1}{k}}\right]\sqrt{\left(\frac{2k}{k-1}\right)\left(\frac{P_0}{\rho_0}\right)\left[1-\left(\frac{P_i}{P_0}\right)^{\frac{k-1}{k}}\right]} \quad (2)$$

Figure 5:
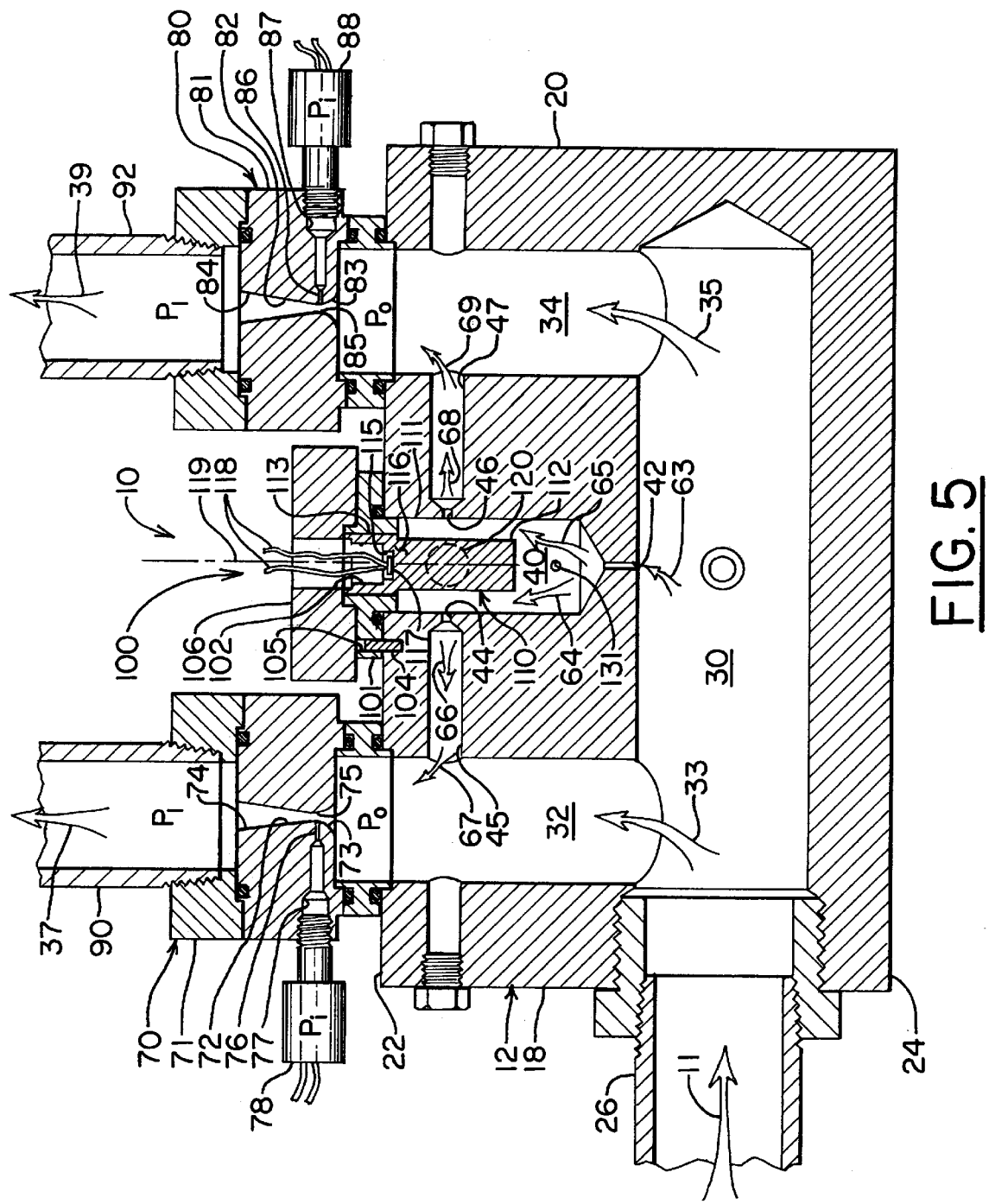
FIG. 5 is a cross-sectional view of the densitometer housing taken along line 5—5 of FIG. 3 showing the densitometer mounted in the housing and the sonic nozzle mass flow meters mounted on the housing.

The throat pressures $P_i$ in the respective nozzles 72, 82 can be measured by pressure transducers 78, 88 mounted in bores 77, 87 in nozzle housings 71, 81 via tap bores 76, 86, as shown in FIG. 5 and as described in more detail in U.S. Pat. No. 5,564,306. The upstream pressure $P_o$ can be measured in any of several locations, preferably through a tap bore 131 into sample chamber 40, as will be described in more detail below.

Figure 6:
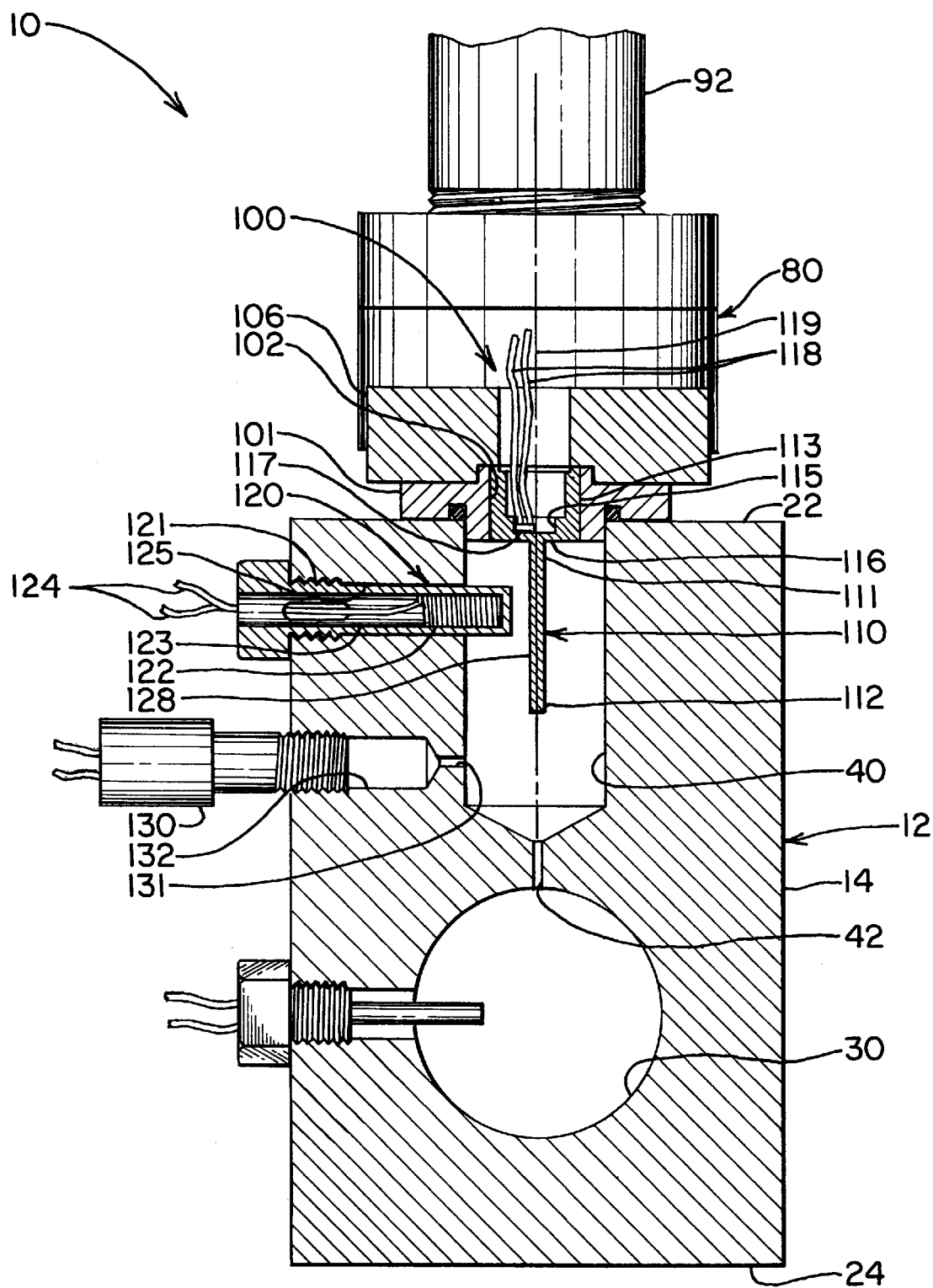
FIG. 6 is a cross-sectional view of the densitometer housing taken along line 6—6 of FIGS. 2 and 4 showing the densitometer and driver mounted in the housing.

The density $\rho_o$ at the pressure $P_o$ upstream of the nozzles 72, 82 for use in determining mass flow rate $\dot{m}$ can be determined according to this invention by the densitometer assembly 100 as best seen in FIGS. 5–6. The densitometer assembly 100 comprises essentially a vane 110 extending into a sample plenum 40, a driver assembly 120 for imparting vibratory motion to the vane 110, and a vibration detector 117 for detecting the vibratory motion of the vane 110. As will be explained in more detail below, the density $\rho_o$ of the gas in sample plenum 40 affects the vibration resonant frequency $f_r$ of the vane 110. Therefore, the density $\rho_o$ of gas in the sample plenum 40 can be determined as a function of the resonant frequency $f_r$ of the vane 110, which can be detected with the vibration detector 117. If the density $\rho_o$ of the gas in the sample plenum 40 changes, the resonant frequency of the vane 110 will also change, and the change can be detected by the vibration detector 117 and an appropriate electric circuit as will be described in more detail below.

As mentioned above, if the density $\rho_o$ of the gas is to be used in the determination of mass flow rate $\dot{m}$ of the gas flowing through either the first sonic nozzle 72 or the second sonic nozzle 82 according equation (2), the density $\rho_o$ has to be measured at substantially the same pressure $P_o$ as the gas in the respective first staging plenum 32 or second staging plenum 34. In ideal conditions where there was no noise, extraneous vibrations, turbulences, or depositions in the gas or the gas pipe, a very sensitive densitometer apparatus could be positioned directly in the manifold chamber 30 or in one or both of the staging plenums 32, 34 to get an accurate density $\rho_o$ measurement at the staging pressure $P_o$ immediately upstream of the sonic nozzle 72 or 82. However, such ideal quiescent conditions seldom prevail, especially, for example, in compressed natural gas (CNG) dispenser applications.

The vane 100 mounted in a cantilevered manner with its proximal end 111 anchored rigidly to a mounting ring 101 and its distal end 112 free to move, as shown in FIGS. 5 and 6, is a simple structure to vibrate. It is also very sensitive to changes in density of the gas environment in which it is positioned, and the constant values of the cantilevered vane that are fixed by such physical characteristics of the vane material as composition, size, shape, and other physical attributes, which values are needed to determine density $\rho_o$ from vane vibration measurements, are relatively easy to determine empirically. The structure of a cantilevered vane is also easy and relatively inexpensive to manufacture. Therefore, the cantilevered vane 100 has the sensitivity and accuracy needed for such mass flow rate $\dot{m}$ determinations as described above for natural gas dispenser and other gas density measurement applications at about one-sixth the cost of other commercially available densitometers that have sufficient sensitivity and accuracy for this application. However, a cantilevered vane structure is not suited for use in a gas flow environment that is subject to frequent and substantial noise, extraneous vibrations and system resonances, turbulence, depositions, and the like. Such extraneous conditions, which are common in natural gas dispenser systems, would throw the cantilevered vane into an unstable condition in which accurate vibrations indicative of the gas density $\rho_o$ would be impossible or at least impractical to detect and measure. Therefore, for purposes of this invention, the sample plenum 40 is provided to position the cantilevered vane 110 in an environment that has substantially the same upstream pressure $P_o$ and density $\rho_o$ as the gas in the staging plenums 32, 34, but which his sufficiently isolated or insulated from the noises, extraneous vibrations and system resonances, turbulence, and depositions in the normal gas flow to avoid instabilities in the vane 110 vibrations that would make detections of resonant frequency $f_r$ changes that are indicative of gas density $\rho_o$ changes impossible or impractical to detect. This sample plenum 40 of this invention is a significant feature that contributes to the feasibility of using a relatively simple, inexpensive, accurate, and dependable cantilevered vane 110 for gas density $\rho_o$ determinations for natural gas dispenser applications.

The sample plenum 40 as shown in FIGS. 5–6 is bored into housing 12, preferably, but not necessarily, between the first staging plenum 32 and the second staging plenum 34 and preferably, but not necessarily, in close proximity to the manifold bore 30. A very small diameter sample inlet duct 42 connects the sample plenum 40 to the manifold bore 30, so that a small sample of the gas flowing through manifold bore 30 is diverted by the sample inlet duct 42 into the sample plenum 40, as indicated by the arrows 63, 64, 65. A first outlet conduit 45 is provided to conduct the gas from the sample plenum 40 to the first staging plenum 32, as indicated by arrows 66, 67, and a second outlet conduit 47 is provided to conduct the gas from the sample plenum 40 to the second staging plenum 34, as indicated by arrows 68, 69. A small diameter first outlet duct 44 connects the first outlet conduit 45 to the sample plenum 40, and a small diameter second outlet duct 46 connects the second outlet conduit 47 to the sample plenum 40.

The flow of gas through staging plenums 32, 34 as indicated by arrows 33, 35 in FIG. 5 tends to draw gas flow through the sample plenum 40 and respective outlet conduits 45, 47 according to the well-known Bernoulli's principle, which keeps the sample of gas in sample plenum 40 refreshed and substantially the same composition and temperature as the gas flowing through staging plenums 32, 34. However, the small sizes of the inlet duct 32 and outlet ducts 44, 46 in relation to the manifold chamber 30 and staging plenums 32, 34 are affective to dampen or diminish intensities and fluctuations due to turbulences, shock waves or noises, and sudden pressure changes that occur in the gas flow in manifold chamber 30 and staging plenums 32, 34 before they reach the sample plenum 40 where they could affect adversely the vibrational stabilities of the vane 110. However, the inlet duct 42 and outlet ducts 44, 46 are not so small as to create any significant pressure differential between the sample plenum 40 and the staging plenums 32, 34 so that the pressure in the sample plenum 40 remains substantially the same as the pressure $P_o$ in the staging plenums 32, 34 upstream of the respective sonic nozzles 72, 82. Therefore, the gas density $\rho_o$ measurements by the vane 110 in sample plenum 40 are made at virtually the same pressures $P_o$ in the staging plenums 32, 34 immediately upstream of the sonic nozzles 72, 82, which is required for accurate mass flow rate $\dot{m}$ measurements according to equation (2) as described above.

Figure 4:
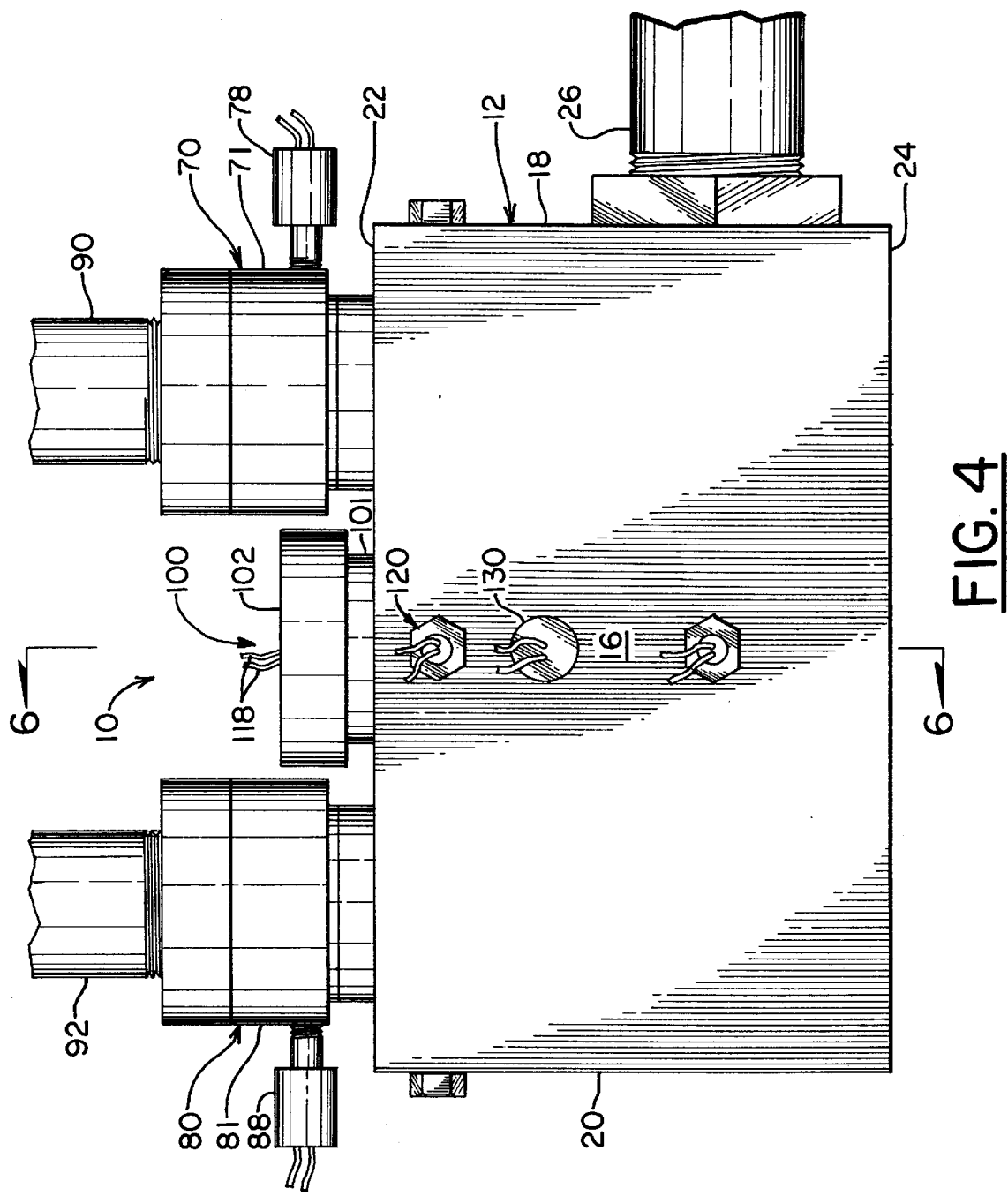
FIG. 4 rear elevation view of the densitometer housing of FIG. 1.

In general, each staging plenum 32, 34 has to be large enough so that the pressure $P_o$ is substantially a stagnant pressure rather than a flowing pressure, even though gas obviously flows through each staging plenum 32, 34 from the manifold chamber 30 to the respective sonic nozzles 72, 82. For the gas flowing through each staging plenum 32, 34 to be sufficiently slow to have a stagnant pressure $P_o$ rather than a flowing pressure, the ASME/ANSI recommendations are that each staging plenum should have a diameter at least four (4) times the diameter of the throat. The sample plenum 40 has to be large enough to accommodate the vane 110 and large enough in relation to the inlet duct 42 and outlet ducts 44, 46 to substantially isolate the gas sample in the sample plenum from noises, shocks and rapid vibratory fluctuations, turbulences, and depositions as explained above, but not so large in relation to the inlet duct 42 and outlet ducts 44, 46 that the composition of the gas sample in the sample plenum 40 changes too slowly to be representative of the gas flowing through the sonic nozzles 72, 82. A sample plenum 40 with a volume in the range of at least about 25 to 75 percent of the volume of a staging plenum 32, 34 (preferably about 50 percent). A ratio of the sample plenum 40 volume $V_s$ to cross-sectional area $A_I$ of inlet duct 42 (using the same linear measurement unit) in the range of about 50:1 to 200:1 (preferably about 125:1) with the cross-sectional area of each outlet duct 44, 46 being about the same as $A_I$ is sufficient for these purposes. For example, but not for limitation, the manifold chamber 30 can be about 2-inches (5.08 cm) in diameter and about 8-inches (19.42 cm) long; each staging plenum 32, 34 can be about 1⅜-inches (3.4925 cm) diameter and about 2¾-inches (5.08 cm) deep; the sample plenum 40 can be about 1-inch diameter (2.54 cm) and about 2½-inches deep; each outlet conduit can be about ⅜-inch diameter and about 1½-inches long; the inlet duct 42 can be about ¹⁄₁₆-inch diameter and about ⅓-inch long; and each outlet duct 44, 46 can be about ¹⁄₁₆-inch diameter and about ⅛-inch long. In this kind of structure and gas flow environment, there is a very slight pressure differential (a few inches of water) between the sample plenum 40 and the staging plenums 32, 34, which is enough to create sufficient gas flow through the sample plenum 40 to remain very representative of the gas flowing through the staging plenums 32, 34. However, a few inches of water (a fraction of a pound per square inch) is very insubstantial in relation to several thousand pounds per square inch that is the normal gas pressure. Therefore, pressure $P_o$ measured in the sample plenum 40 is substantially the same as pressure $P_o$ in staging plenums 32, 34. The pressure $P_o$ can be measured by a pressure transducer 130 mounted in a bore 131, which is in communication with sample chamber 40 via a tap bore 131, as best seen in FIGS. 4–6.

The vane 110 is preferably, but not necessarily, comprised of a material for which the modulus of elasticity is independent of temperature so that the resonant frequency is a function of the density $\rho_o$ of the gas in the sample plenum 40 but independent of temperature. The metal alloy NiSPAN3 is such a material, and when the vane 110 is made of NiSPAN3, it makes measuring the density $\rho_o$ of the gas by measuring the resonant frequency $f_r$ of the vane 110 a relatively easy matter. In general, resonant frequency $f_r$ of the vane 110 is related to density $\rho_o$ of the gas in the sample plenum 40 around the vane 110 by a second order polynomial of the form $$\rho_o = A + BP + CP^2 \qquad (3)$$

where P is period of oscillations or vibration cycles and A, B, and C are constants that are related to the composition, shape, and size of the vane 110 and other physical parameters of the system. Such constants A, B, and C can be determined empiracally for any particular vane and densitometer structure, composition, shape, and size. The period P of vibratory movement is the inverse of frequency. Therefore, as the density $\rho_o$ of the gas increases, the resonant frequency $f_r$ of the vane 110 decreases and vice versa according to the relationship $$\rho_0 = A + \frac{B}{f_r} + \frac{C}{f_r^2} \qquad (4)$$

For example, with an NiSPAN3 alloy vane 110 as described above with a width of about 0.500 inch thickness of about 0.015 inch, and cantilevered length of about 1.250 inches, the resonant frequency $f_r$ is approximately 2,000 Hz in a vacuum, but in a gas pressure of about 3,000 p.s.i., the resonant frequency $f_r$ is approximately 1,500 Hz. In compressed natural gas flow in a typical dispensing operation, the resonant frequency $f_r$ is usually about 1,750 Hz and only varies about 200 p.s.i. when gas ranges from 1,000 Hz to 5,000 p.s.i.

As best seen in FIGS. 5 and 6, the vane 110 is preferably, but not necessarily, cantilevered longitudinally along a longitudinal axis 119 from a cup-shaped base 113. The cup-shaped base 113 is anchored in a vane mounting ring 101 by inserting and fastening the cup-shaped base 113 into a bore 102 extending through the mounting ring 101. A guide bore 105 laterally offset from the bore 102 in mounting ring 101 is adapted for receiving a guide pin 104 that protrudes from the top surface 22 of the housing 12 for ensuring that the vane 112 is mounted in proper orientation with respect to the driver assembly 120, as will be explained in more detail below. A retainer 106 is positioned over the vane mounting ring 101 for fastening the mounting ring 101 and vane in place on the housing 12. Any suitable fastener device such as bolts (not shown), welding (not shown) or other device can be used to fasten the retainer 106 to the housing as would be well-known to persons skilled in the art.

The vibrator detector 117, such as a piezoelectric crystal, strain gauge, or other suitable vibration detector system, is preferably mounted on a thinner or weaked portion 116 of the base 113 that is created by a recess 115 in the interior of the cup-shaped base 113 toward the proximal end 111 of vane 110. The weaked portion 116 accommodates flexure or strain in that portion of the base 113 from vane 110 movement, thus enhances vane vibration detection by the vibration detector 117. The preferred vibration detector 117 is a piezoelectric crystal adhered by epoxy to the weaked portion 116. It is also preferred that the vibration detector is mounted offset to one side of the center line or longitudinal axis 119 of the vane 110 to optimize detection of strain or flexure caused by movement or vibratory motion of the vane 110.

Vibratory motion is imparted to the vane 110 by a driver assembly 120 positioned adjacent the vane 110 in the sample plenum 40. As best seen in FIG. 6, the driver assembly 110 comprises an elongated threaded sleeve 121 inserted through a bore 125 in housing 12 that extends from the back side 16 into the sample plenum. An electromagnetic coil 122 mounted on the end of a ferrule 123 in the sleeve 121 is thereby positioned in proximity to the wide surface 128 of the vane 110. An oscillating electric current applied to the coil 122 via wires 124 induce an oscillating magnetic field that interacts with the vane 110 to cause the vane 110 to vibrate. An electric signal detector and feedback loop, preferably a phase locked loop, detects the resonant frequency $f_r$ of the vane 110 and drives the electric current in the coil to oscillate at the resonant frequency $f_r$. Since the resonant frequency $f_r$ is a function of the density $\rho_o$ of the gas in the sample plenum 40 surrounding the vane 110, the resonant frequency is used to determine the density $\rho_o$ of the gas.

As previously discussed above, the resonant frequency $f_r$ of the vane 110 is related to the density of the gas in the supply plenum. Therefore, in order to determine the density of the gas in the sample plenum 40, the resonant frequency $f_r$ of the vane 110 must first be determined. When the vane 110 vibrates, the vibrations are detected by the vibration detector 117 connected to the vane 110. The vibration detector 117 generates an electric signal on the wires 118 that is representative of the frequency of the vibrations of the vane 110.

The resonant frequency $f_r$ of the vane 110 is determined by applying a magnetic field against the vane 110. The magnetic field is generated by the driver assembly 120. When the frequency of the magnetic field created by the driver assembly 120 and applied against the vane 110 is such that it is equal to the resonant frequency $f_r$ of the vibrations of the vane 110, the amplitude of the vibrations of the vane 110 will be maximized and, as a result, the amplitude of the electric signal created on the wires 118 by the vibration detector 117 will also be maximized. A change of resonant frequency $f_r$ in the vane 110 in relation to a change in the density of the gas in the supply plenum 40 is easy to measure, therefore, and any changes in the density of the gas in the supply plenum 40 can be detected almost immediately and accurately by detecting the change in the resonant frequency $f_r$ of the vane 110.

The vane 110 and the driver assembly 120 are connected together in a feedback circuit such that, essentially, the frequency of the electric signal on the wires 118 generated by the vibration detector 117 is compared against the frequency of the electric signal on the wires 124 that energizes the driver assembly 120. The frequency of the electric signal on the wires 124 is adjusted by the feedback circuit until it is equal to the frequency of the electric signal on the wires 118. The frequency of the electric signal on the wires 118, which is generally between 1,550 hertz and 1,950 hertz, is then measured and used with the equations provided above to determine the density of the gas in the sample plenum 40.

Figure 7:
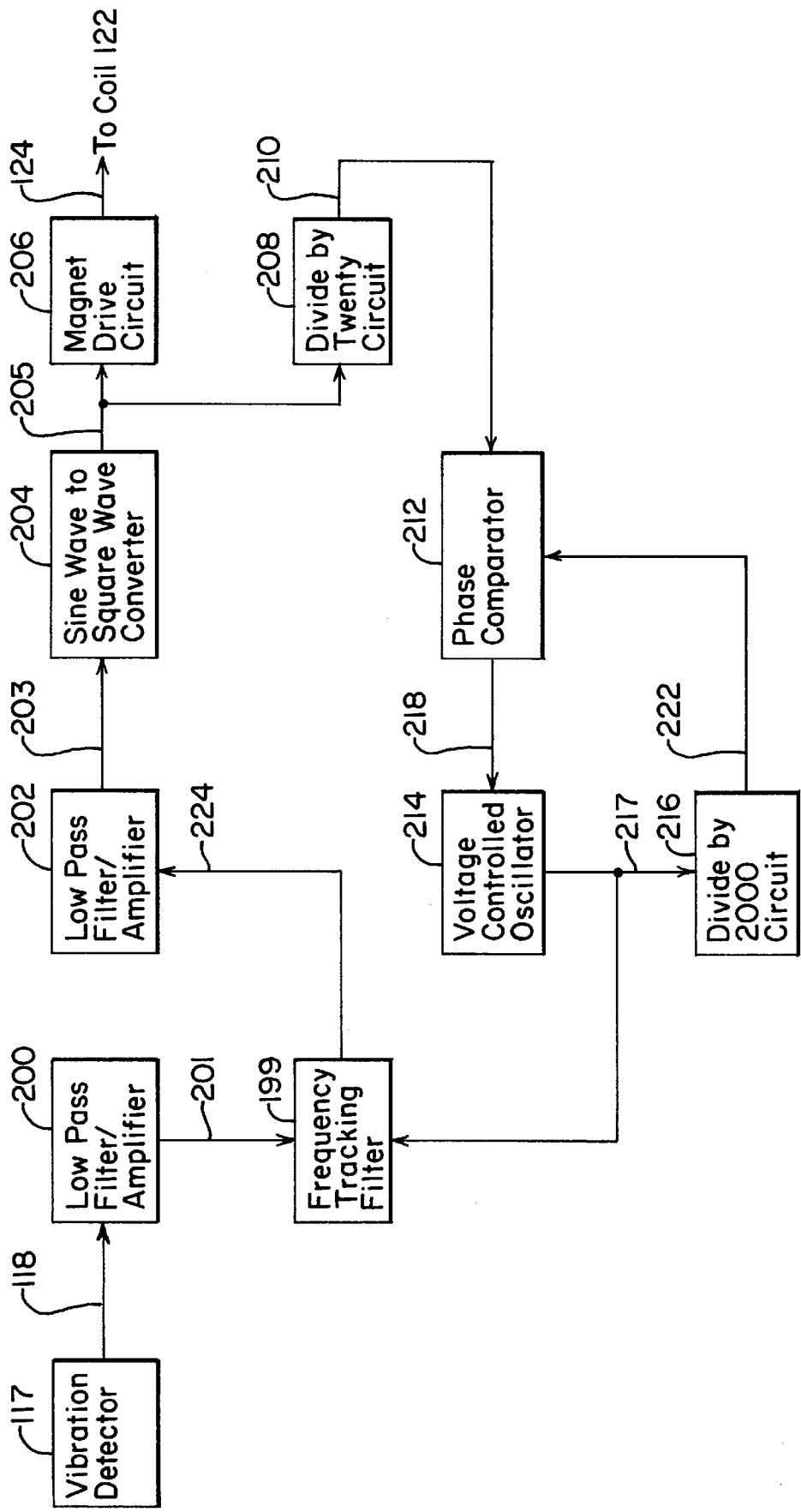
FIG. 7 is a finctional block diagram of the feedback circuit connecting the vane and the driver assembly of FIG. 6.
Figure 8A:
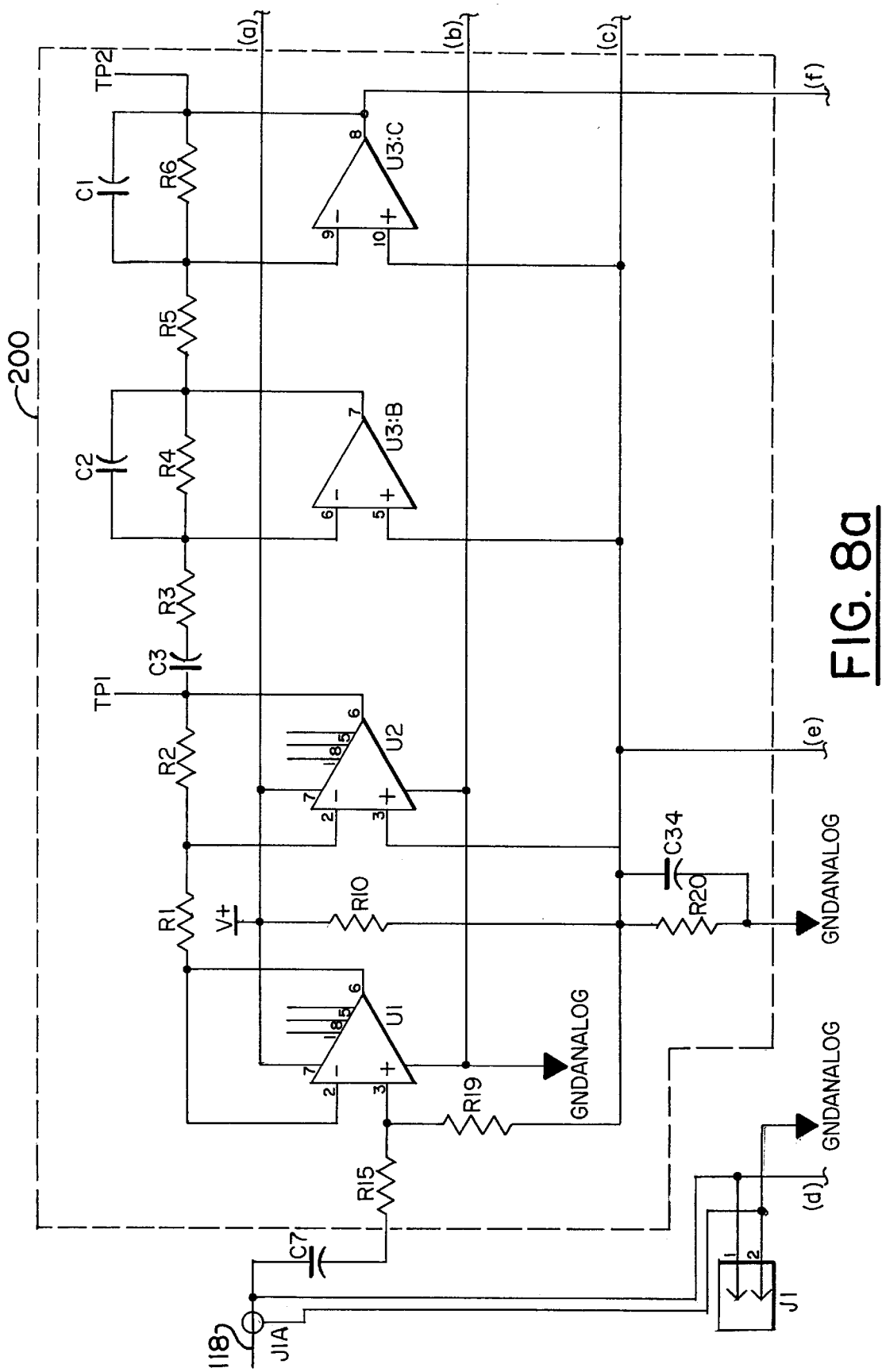
FIG. 8 is an exemplary schematic diagram of the function block diagram of FIG. 7.
Figure 8B:
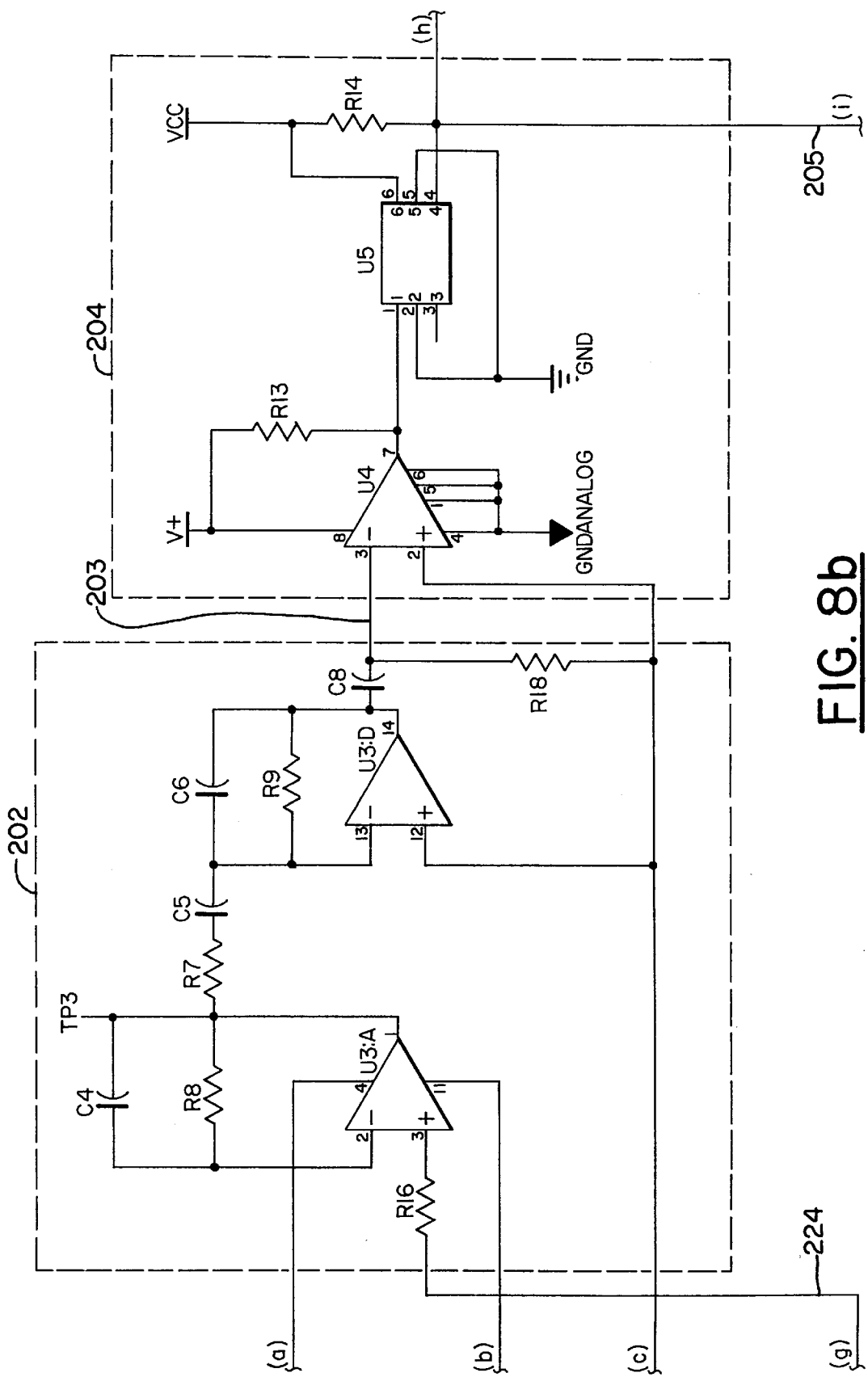
Figure 8C:
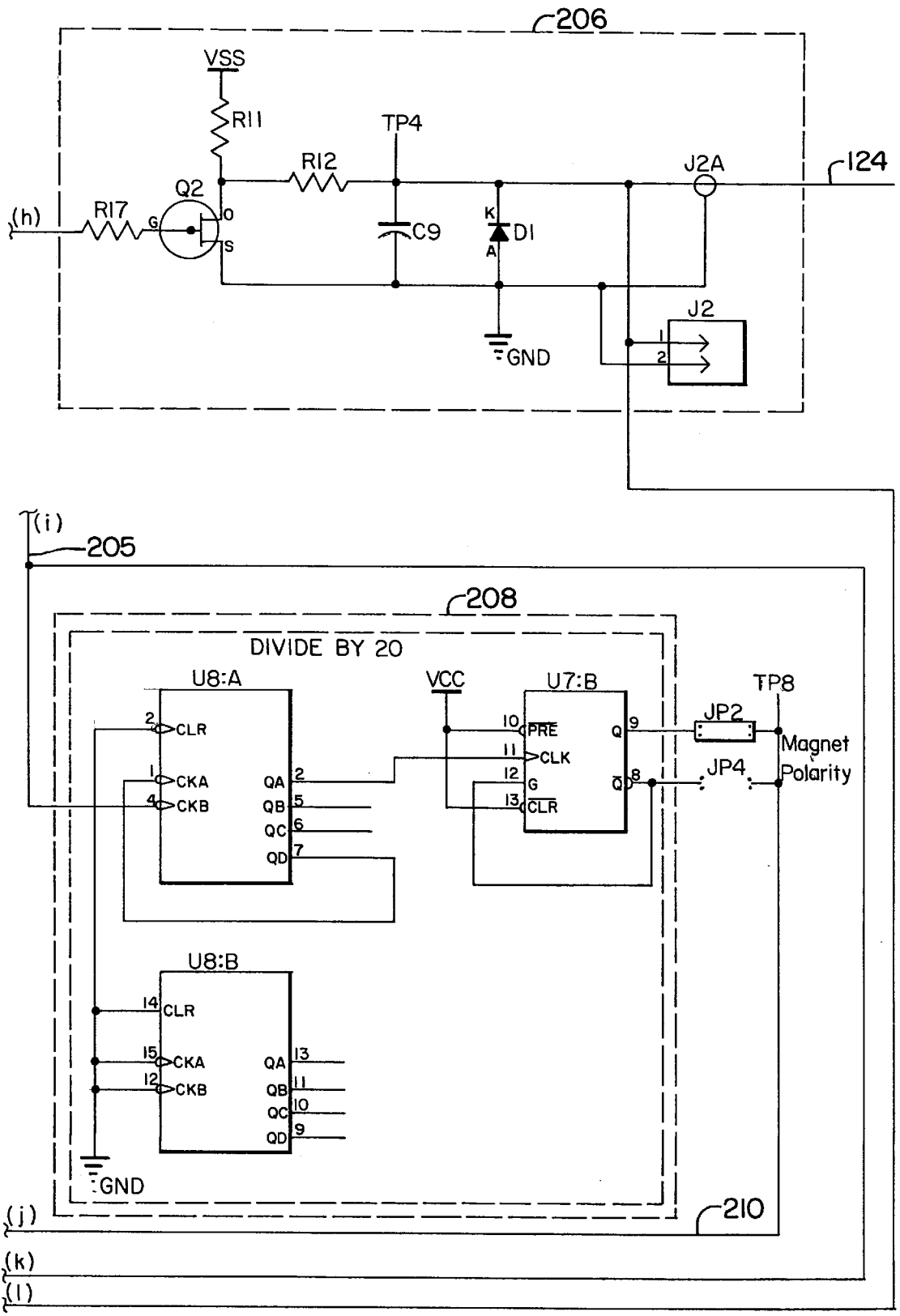
Figure 8D:
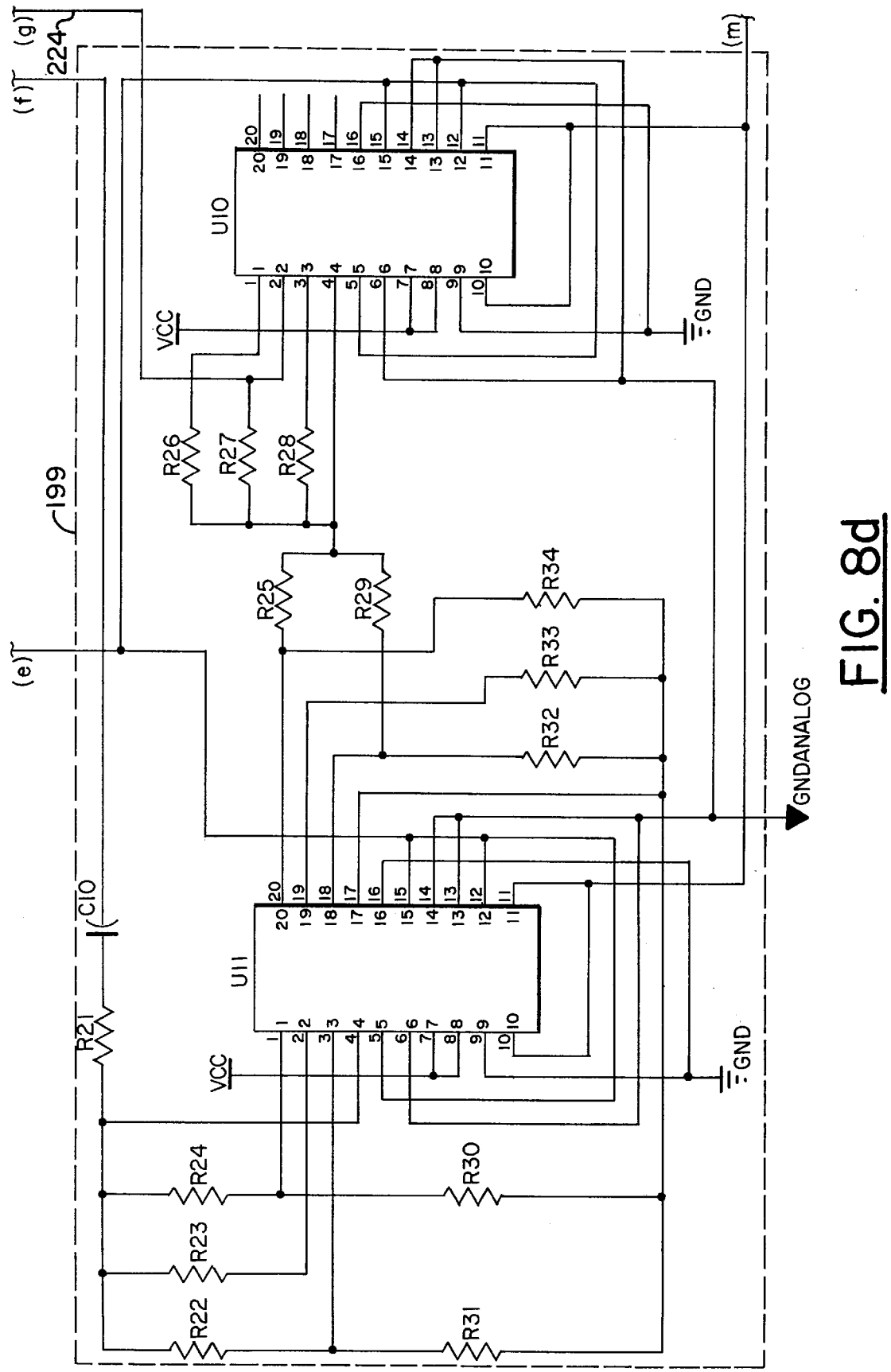
Figure 8E:
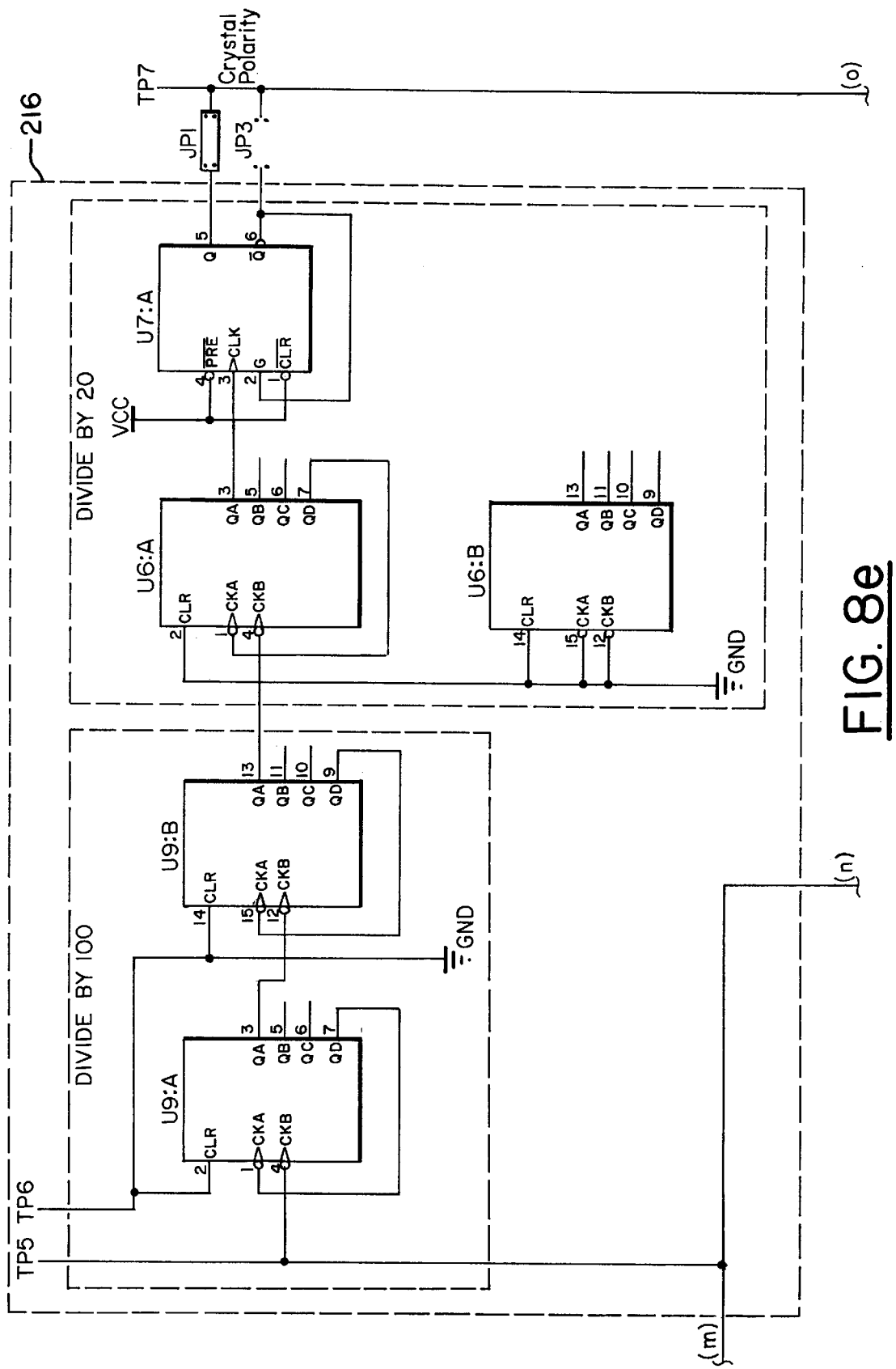
Figure 8F:
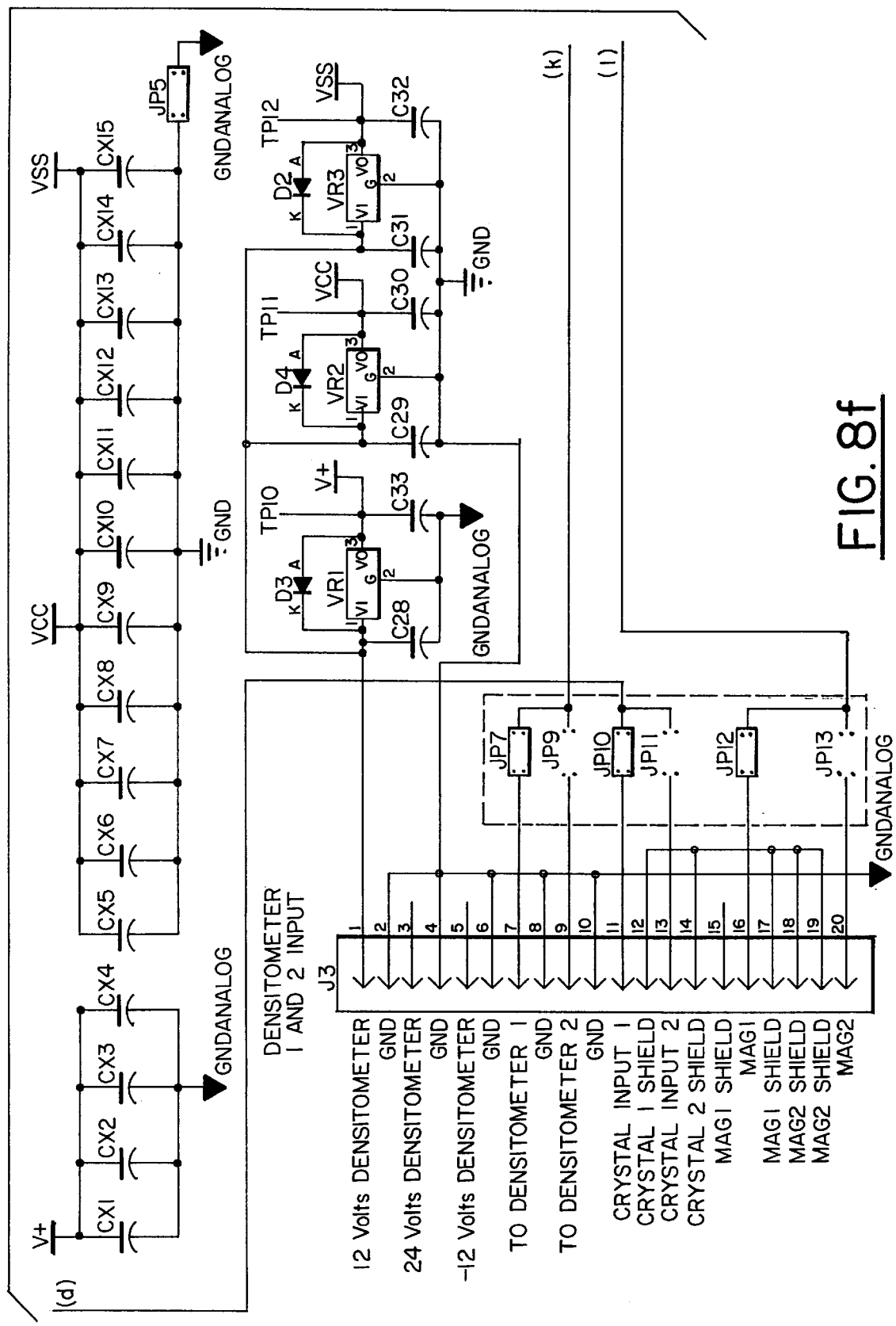
Figure 8G:
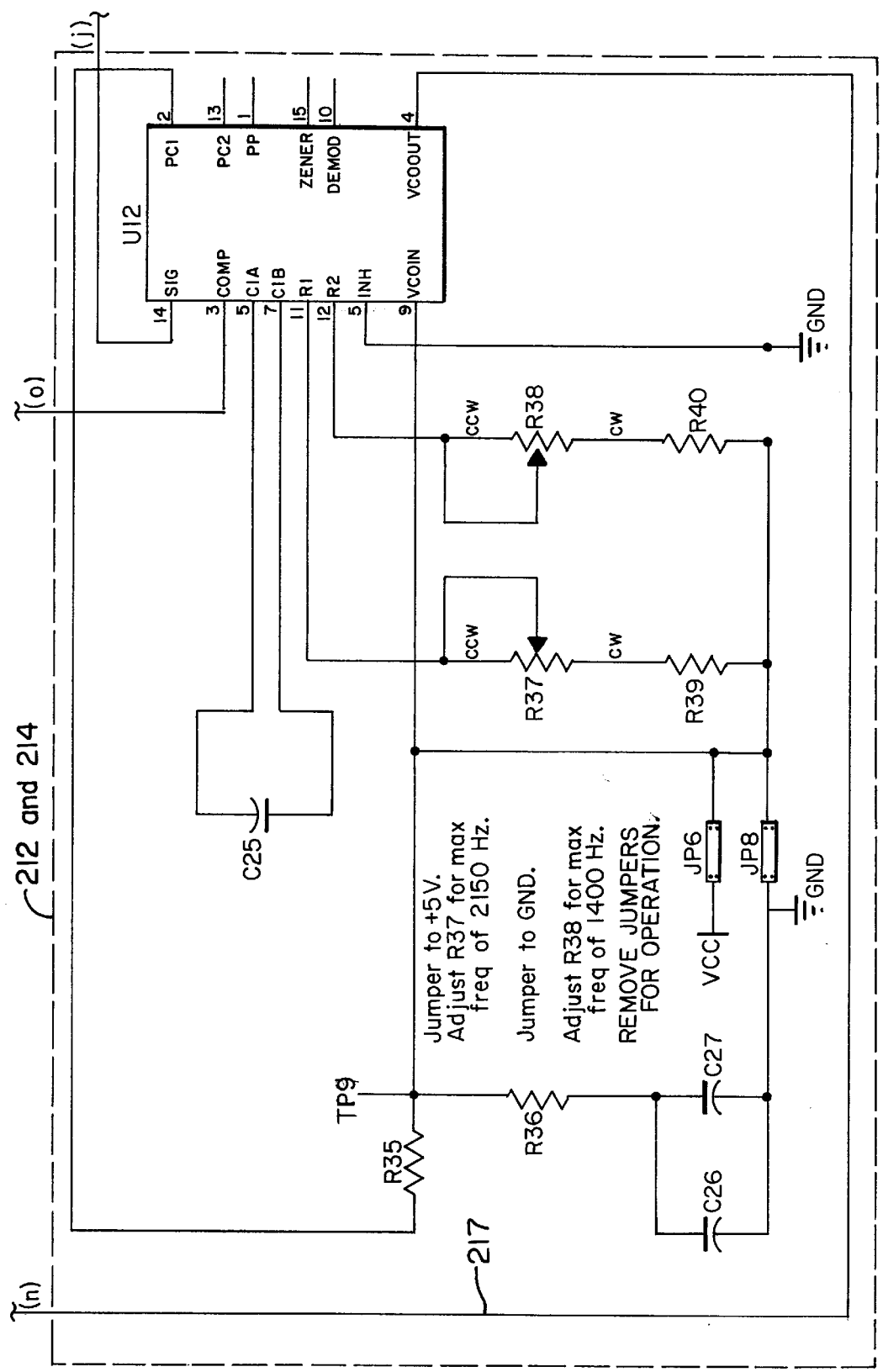

Now referring to FIG. 7, the general operation of the feedback circuit connecting the vane 110 and the driver assembly 120 will now be discussed in more detail. Vibrations of the vane 110 created by gas in the sample plenum 40 causes the vibration detector 117 to create an electric sine-wave voltage signal on the wires 118. The electric voltage signal created by the vibration detector 117 on the wires 118 is an input signal to the low pass filter/amplifier 200. The output electric sine-wave voltage signal from the low pass filter/amplifier 200 on the lead 201 is an input signal to the frequency tracking filter 199 which provides an input sine-wave voltage signal to the low pass filter/amplifier 202 on the lead 224, as will be discussed in more detail below.

The output electric sine-wave voltage signal from the low pass filter/amplifier 202 on the lead 203 is an input signal to the converter 204 which converts the sine-wave signal on the lead 203 to a square-wave voltage signal on the lead 205. The square-wave voltage signal on the lead 205 is an input signal to the magnet drive circuit 206 which activates a switch in the magnetic drive circuit 206 that provides the electric voltage signal on the wires 124 that energizes the drive assembly 120 and, as a result, the magnetic field applied to the vane 110.

The square wave voltage signal on the lead 205 is also an input signal to the divider circuit 208 which divides the frequency of the electric voltage signal on the lead 205 by twenty. Since the frequency of the electric signal on the lead 205 is generally within 200 hertz of 1,750 hertz (i.e., between 1,550 hertz and 1,950 hertz), the frequency of the electric voltage signal on the lead 210 varies around 87.5 hertz. The frequency reduction is used to help the phase comparator 212 and the voltage controlled oscillator 214 lock onto the frequency of the electric voltage signal created by the vane 110.

The output voltage signal from the divider circuit 208 on the lead 210 is an input signal to the phase comparator 212. The phase comparator 212, the voltage controlled oscillator 214, and the divider circuit 216 work together as a phase-locked loop to create a reference signal on the lead 217. The output voltage signal from the voltage controlled oscillator 214 on the lead 217 has a frequency that varies about approximately 175,000 hertz. The divider circuit 216 divides the frequency of the voltage signal on the lead 217 by two thousand and creates a voltage signal on the lead 222 that is in input signal to the phase comparator 212. Therefore, the frequencies of the voltage signals on both the lead 210 and the lead 222 are approximately 87.5 hertz.

The output voltage signal from the voltage controlled oscillator 214 on the lead 217 is also an input reference signal to the frequency tracking filter 199. The frequency tracking filter 199 uses and compares the electric voltage signals on the leads 201, 217 to create the input signal to the low pass filter/amplifier 202 on the lead 224, as previously discussed above. An exemplary schematic diagram of the functional block diagram of FIG. 7 is provided in FIG. 8.

While the driver is shown to be an electromagnet in the preferred embodiment, any exciter that imparts energy to the vane to induce vibration can work with this invention. Also, while a phase locked loop resonant frequency detector and driver circuit is preferred, other types of detection and driver circuits, such as a frequency sweeping and peak amplitude detecting circuit to detect resonant frequency of the vane similar to that described in U.S. Pat. No. 4,679,947, which is also incorporated herein by reference, can be used.

The foregoing description is considered as illustrative only of the principles of the invention. Furthermore, since numerous modifications and changes will readily occur to those skilled in the art, it is not desired to limit the invention to the exact construction and process shown as described above. Accordingly, all suitable modifications and equivalents may be resorted to falling within the scope of the invention as defined by the claims which follow.

We claim:

1. Densitometer apparatus for use in combination with a mass flow meter for measuring density of gas flowing from a gas supply through the mass flow meter, said densitometer apparatus comprising:

a staging plenum positioned between the gas supply and the mass flow meter, said staging plenum having a volume;

a sample plenum positioned adjacent the staging plenum and having a volume that is at least 25 percent as large as the volume of the staging plenum;

a gas inlet connecting the sample plenum in fluid flow relation with the gas supply and having a cross-sectional area sized such that a ratio of the sample plenum volume to the gas inlet cross-sectional area is not smaller than about 50:1;

a gas outlet extending in fluid flow relation between the sample plenum and the staging plenum upstream from the gas inlet, said gas outlet having a cross-sectional area sized such that a ratio of the sample plenum volume to the gas outlet cross-sectional area is not smaller than about 50:1; and a vibration member positioned in the sample plenum, a vibration driver adjacent the vibration member, and a vibration detector adjacent the vibration member.

2. The densitometer apparatus of claim 1, including a gas supply manifold and wherein said staging plenum and said gas inlet are both connected in fluid flow relation to said manifold.

3. The densitometer apparatus of claim 1, wherein the ratio of the sample plenum volume to the gas inlet cross-sectional area is not larger than about 200:1, and wherein the ratio of the sample plenum volume to the gas outlet cross-sectional area is not larger than about 200:1.

4. The densitometer apparatus of claim 3, wherein the ratio of the sample plenum volume to the gas inlet cross-sectional area is about 125:1.

5. The densitometer apparatus of claim 3, wherein the ratio of the sample plenum volume to the gas outlet cross-sectional area is about 125:1.

6. The densitometer apparatus of claim 1, wherein the volume of the sample plenum is in a range of about 25 to 75 percent as large as the volume of the staging plenum.

7. The densitometer apparatus of claim 6, wherein the volume of the sample plenum is about 50 percent as large as the volume of the staging plenum.

8. The densitometer apparatus of claim 1, wherein the vibration member includes an elongated vane that is cantilever mounted in the sample plenum with a proximal end of said vane fixed and a distal end of said vane free to move.

9. The densitometer apparatus of claim 8, wherein the proximal end of the elongated vane is anchored to a cup-shaped base mounted at one end of the sample plenum in a manner such that the elongated vane extends into the sample plenum.

10. The densitometer apparatus of claim 9, wherein said cup-shaped base has a portion that is thinner than other portions of the cup-shaped base and said proximal end of said vane is anchored to said thinner portion.

11. The densitometer of claim 10, wherein said vibration detector includes a piezoelectric crystal adhered to said thinner portion.

12. The densitometer of claim 11, wherein said elongated vane has a longitudinal axis and said piezoelectric crystal is adhered to said thinner portion offset to one side of the longitudinal axis.

13. Gas metering apparatus, comprising:
  a sonic nozzle with a converging section that converges to a throat that has a throat diameter and with a diverging section that diverges from the throat;
  a staging plenum in fluid flow communication with a gas supply, said staging plenum having a volume that is positioned between the converging section of the sonic nozzle and the gas supply, said staging plenum having a diameter that is at least four times as large as the throat diameter;
  a sample plenum positioned adjacent the staging plenum and having a volume that is at least 25 percent as large as the staging plenum volume;
  a gas inlet connecting the sample plenum in fluid flow relation with the gas supply and having a cross-sectional area that is sized such that a ratio of the sample plenum volume to the gas inlet cross-sectional area is not smaller than about 50:1;
  a gas outlet extending in fluid flow relation between the sample plenum and the staging plenum upstream from the gas inlet, said gas outlet having a cross-sectional area sized such that a ratio of the sample plenum volume to the gas outlet cross-sectional area is not smaller than about 50:1; and
  gas density measuring apparatus positioned in said sample plenum.

14. The gas metering apparatus of claim 13, including a gas supply manifold and wherein said staging plenum and said gas inlet are both connected in fluid flow relation to said manifold.

15. The gas metering apparatus of claim 13, wherein the ratio of the sample plenum volume to the gas inlet cross-sectional area is not larger than about 200:1, and wherein the ratio of the sample plenum volume to the gas outlet cross-sectional area is not larger than about 200:1.

16. The gas metering apparatus of claim 15, wherein the ratio of the sample plenum volume to the gas inlet cross-sectional area is about 125:1.

17. The gas metering apparatus of claim 15, wherein the ratio of the sample plenum volume to the gas outlet cross-sectional area is about 125:1.

18. The gas metering apparatus of claim 13, wherein the volume of the sample plenum is in a range of about 25 to 75 percent as large as the volume of the staging plenum.

19. The gas metering apparatus of claim 18, wherein the volume of the sample plenum is about 50 percent as large as the volume of the staging plenum.

20. The gas metering apparatus of claim 13, wherein the gas density measuring apparatus includes an elongated vane that is cantilever mounted in the sample plenum with a proximal end of said vane fixed and a distal end of said vane free to move.

21. The gas metering apparatus of claim 20, wherein the proximal end of the elongated vane is anchored to a cup-shaped base mounted at one end of the sample plenum in a manner such that the elongated vane extends into the sample plenum.

22. The gas metering apparatus of claim 21, wherein said cup-shaped base has a portion that is thinner than other portions of the cup-shaped base and said proximal end of said vane is anchored to said thinner portion.

23. The gas metering of claim 22, wherein said vibration detector includes a piezoelectric crystal adhered to said thinner portion.

24. The gas metering of claim 23, wherein said elongated vane has a longitudinal axis and said piezoelectric crystal is adhered to said thinner portion offset to one side of the longitudinal axis.

25. Densitometer apparatus for use in combination with mass flow meters for measuring density of gas flowing from a gas supply through the mass flow meters, said densitometer apparatus comprising:
  a manifold connected in fluid flow relation to the gas supply;
  a first staging plenum positioned in fluid flow relation between the manifold and a first mass flow meter, said first staging plenum having a volume;
  a second staging plenum positioned in fluid flow relation between the manifold and a second mass flow meter, said second staging plenum having a volume;
  a sample plenum positioned between the first staging plenum and the second staging plenum and having a volume;
  a gas inlet extending in fluid flow relation between the manifold and the gas inlet, said gas inlet having a cross-sectional area sized such that a ratio of the sample plenum volume to the gas inlet cross-sectional area is not smaller than about 50:1;
  a first gas outlet extending in fluid flow relation between the sample plenum and the first staging plenum, said first gas outlet having a cross-sectional area sized such that a ratio of the sample plenum volume to the first gas outlet cross-sectional area is not smaller than about 50:1;
  a second gas outlet extending in fluid flow relation between the sample plenum and the second staging plenum, said second gas outlet having a cross-sectional area sized such that a ratio of the sample plenum volume to the second gas outlet cross-sectional area is not smaller than about 50:1; and
  a vibration member positioned in the sample plenum, a vibration driver adjacent the vibration member, and a vibration detector adjacent the vibration member.

26. Densitometer apparatus, comprising:
  (A) a body having:
    (i) a manifold bore extending from a first face on the body into said body along a manifold axis;
    (ii) a first staging plenum bore extending from a second face on the body into the body along a first staging plenum axis that intersects said manifold axis, said first staging plenum bore extending into the body for a sufficient distance to intersect said manifold bore;
    (iii) a second staging plenum bore extending from said second face into the body along a second staging plenum axis that intersects said manifold axis, said second staging plenum bore extending into the body for a sufficient distance to intersect said manifold bore;
    (iv) a sample plenum bore extending from said second face into the body along a sample plenum axis positioned between the first staging plenum and the second staging plenum, said sample plenum bore not intersecting said manifold bore;

(v) a gas inlet bore that is smaller in diameter than said sample plenum bore extending from said sample plenum bore to said manifold bore;
(vi) a first gas outlet bore extending between said sample plenum bore and said first staging plenum bore, said first gas outlet bore being smaller in diameter than said sample plenum bore and smaller in diameter than said first staging plenum bore;
(vii) a second gas outlet bore extending between said sample plenum bore and said second staging plenum bore, said second gas outlet bore being smaller in diameter than said sample plenum bore and smaller in diameter than said second staging plenum bore;

(B) a first mass flow meter mounted on said second face of the body in fluid flow relation to said first staging plenum bore;

(C) a second mass flow meter mounted on said second face of the body in fluid flow relation to said second staging plenum bore, and (D) density measuring apparatus mounted on said second face of the body and extending into said sample plenum bore.

27. The densitometer apparatus of claim 26, wherein said sample plenum bore has a volume and said gas inlet bore has a cross-sectional area sized such that a ratio of the sample plenum bore volume to the gas inlet cross-sectional area is not smaller than about 50:1.

28. The densitometer apparatus of claim 27, wherein said first staging plenum bore has a volume and said second staging plenum has a volume, further wherein said sample plenum bore volume is at least 25 percent as large as the first staging plenum bore volume and at least 25 percent as large as the second staging plenum bore volume.

29. The densitometer apparatus of claim 28, wherein the first gas outlet bore is sized to have a cross-sectional area such that a ratio of the sample plenum bore volume to the first gas outlet bore cross-sectional area is not smaller than about 50:1, and wherein the second gas outlet bore is sized to have a cross-sectional area such that a ratio of the sample plenum bore volume to the second gas outlet bore cross-sectional area is not smaller than about 50:1.

\* \* \* \* \*

UNITED STATES PATENT AND TRADEMARK OFFICE
CERTIFICATE OF CORRECTION

PATENT NO : 5,900,534
DATED : May 4, 1999
INVENTOR(S): Miller, et. al.

It is certified that error appears in the above-identified patent and that said Letters Patent is hereby corrected as shown below:

In Column 1, Line 31, Change Cd to $C_d$.

In Column 7, Line 49, Change 200 p.s.i. to 200 Hz.
In Column 7, Line 50, Change 5,000 p.s.i. to 5,000 Hz.

Signed and Sealed this

Sixteenth Day of November, 1999

*Attest:*

Q. TODD DICKINSON

*Attesting Officer*     *Acting Commissioner of Patents and Trademarks*